United States Patent [19]
Bahal et al.

[11] Patent Number: 5,866,154
[45] Date of Patent: Feb. 2, 1999

[54] STABILIZED NALOXONE FORMULATIONS

[75] Inventors: Surendra Mohan Bahal, Wayne, Pa.; Lei-Shu Wu, Wilmington, Del.

[73] Assignee: The DuPont Merck Pharmaceutical Company, Wilmington, Del.

[21] Appl. No.: 673,601

[22] Filed: Jun. 25, 1996

Related U.S. Application Data

[63] Continuation of Ser. No. 319,920, Oct. 7, 1994, abandoned.

[51] Int. Cl.$^6$ ............................... A61F 2/02; A61K 31/70
[52] U.S. Cl. .............................................. 424/423; 514/23
[58] Field of Search ................................. 514/23; 424/423

[56] References Cited

U.S. PATENT DOCUMENTS

| | | | |
|---|---|---|---|
| 4,447,456 | 5/1984 | Ciganek | 546/44 |
| 4,576,930 | 3/1986 | Sugiyama et al. | 514/23 |

*Primary Examiner*—Carlos A. Azpuru
*Attorney, Agent, or Firm*—Karen H. Kondrad

[57] ABSTRACT

Physically and chemically stable pharmaceutical compositions useful for administering naloxone by injection are described. These compositions are essentially aqueous solutions having a pH between 3.0–3.5, and containing naloxone, an acidic or buffer component, a tonicity-adjusting agent, and a stabilizing agent, said composition being optionally sterilized by autoclaving.

9 Claims, 8 Drawing Sheets

Effect of Autoclaving on Naloxone Degradation

Effect of Autoclaving on Noroxymorphone Formation

The degradation of naloxone (Figure 1a) and formation of noroxymorphone (Figure 1b) for nitrogen sparged (1), non-sparged (2), and oxygen sparged (3) samples under autoclaving and non-autoclaving conditions.

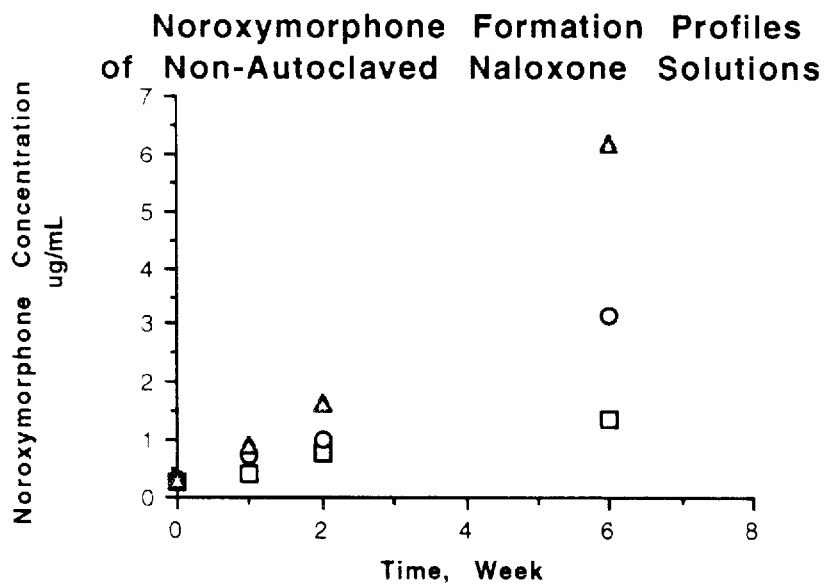
Figure 2  Noroxymorphone formation profiles of non-autoclaved naloxone solutions stored at 60°C.
Δ   Oxygen sparged sample (~100% oxygen in headspace)
O   Non-sparged sample (18% oxygen in headspace)
□   Nitrogen sparged sample (3-5% oxygen in headspace)

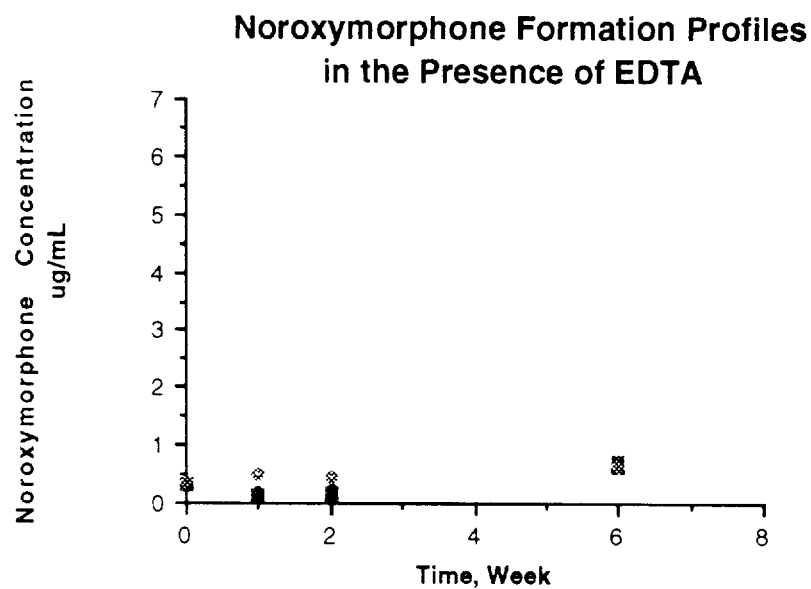
Figure 3  Noroxymorphone formation profiles of solutions with
EDTA added and stored at 60°C.
θ    Nitrogen sparged, non-autoclaved sample
F    Nitrogen sparged, autoclaved sample
n    Non-sparged, non-autoclaved sample
v    Non-sparged, autoclaved sample

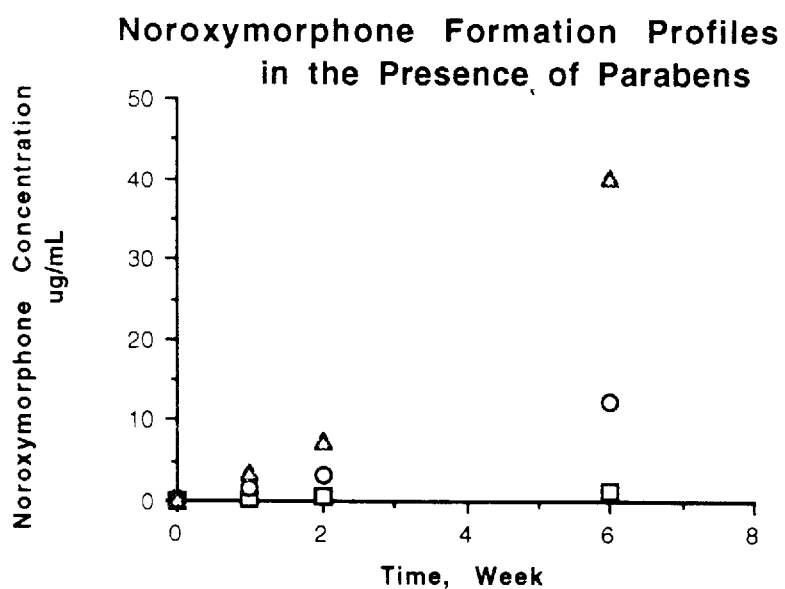
Figure 4  Noroxymorphone formation profiles of samples with parabens added and stored at 60°C.
△  Oxygen sparged sample;
○  Non-sparged sample;
□  Nitrogen sparged sample.

Effect of sodium edetate Concentration on Stability of Autoclaved and Non-Autoclaved Nitrogen Purged Naloxone solutions
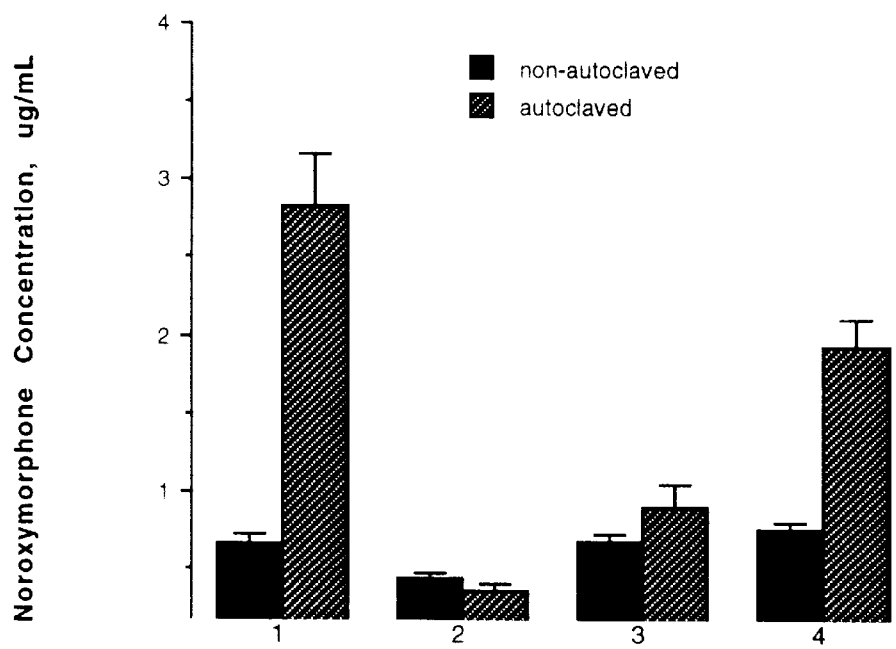
Figure 5 Noroxymorphone formation for naloxone solutions at different sodium edetate concentrations with nitrogen purged before and after autoclaving. 1- no sodium edetate added; 2- 0.001% sodium edetate; 3- 0.0001% sodium edetate; 4- 0.00005% sodium edetate.

Effect of sodium edetate Concentration on Stability of Autoclaved and Non-Autoclaved Naloxone solutions without Nitrogen Purging

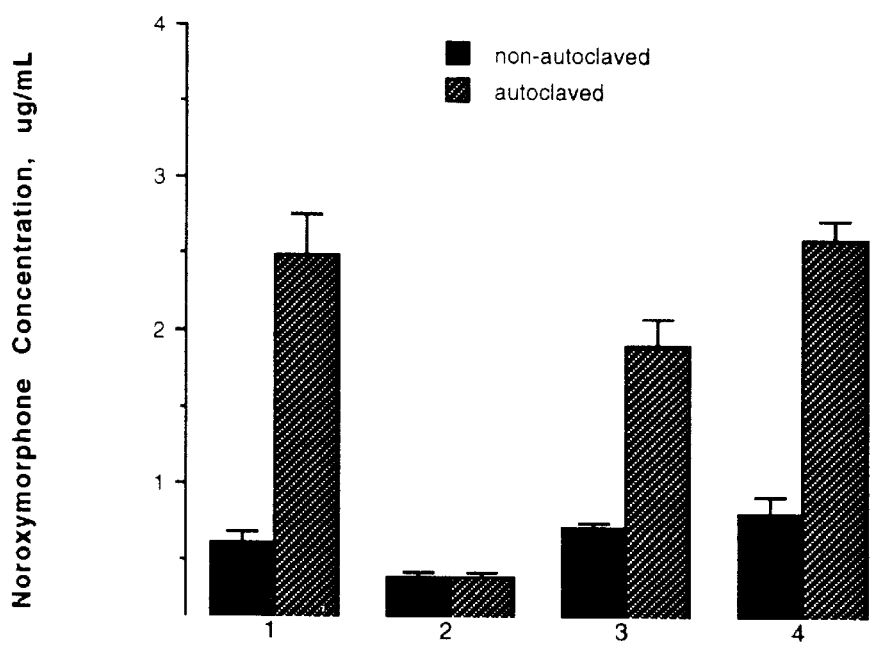

Figure 6 Noroxymorphone formation for naloxone solutions at different sodium edetate concentrations without nitrogen purged before and after autoclaving. 1- no sodium edetate added; 2- 0.001% sodium edetate; 3-0.0001% sodium edetate; 4- 0.00005% sodium edetate.

Effect of Sodium edetate Concentration on Stability of Nitrogen Purged Naloxone Solutions at 60°C
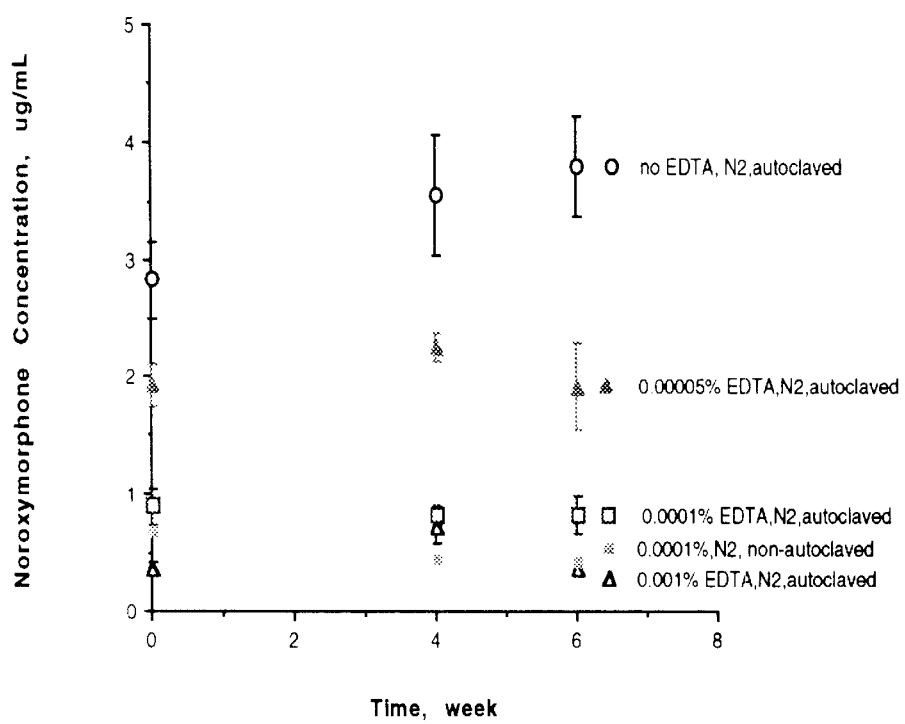
Figure 7  Noroxymorphone formation profiles of nitrogen purged, autoclaved naloxone solutions with different sodium edetate concentration and stored at 60°C.

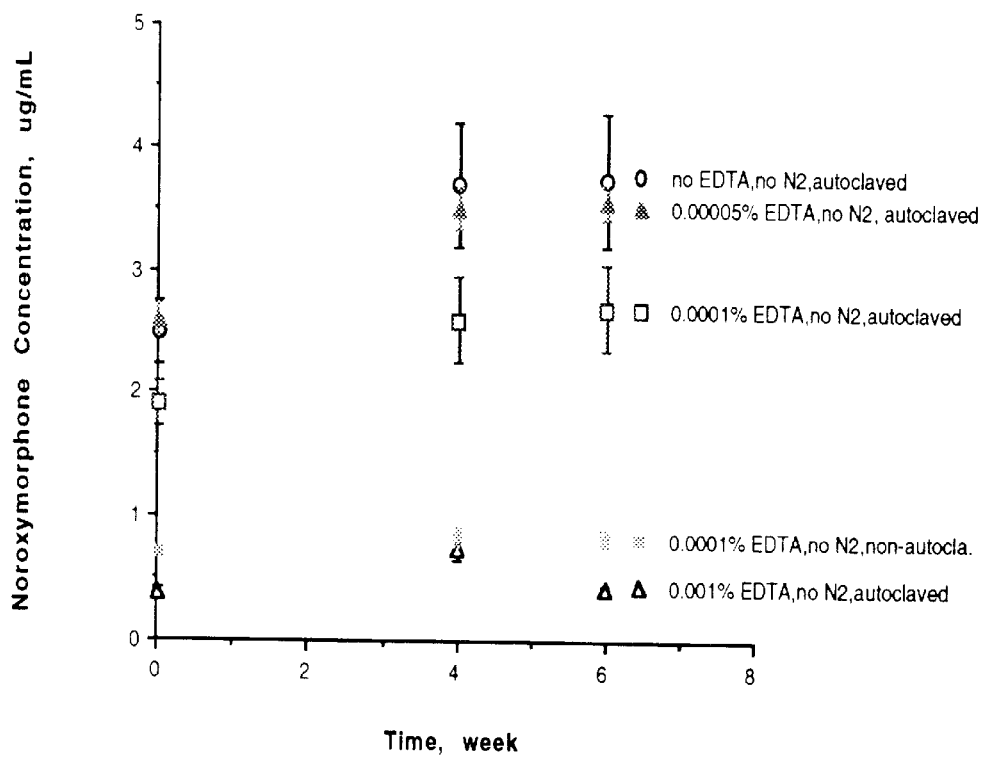
Figure 8  Noroxymorphone formation profiles of non-nitrogen purged, naloxone solutions with different sodium edetate concentration and stored at 60°C.

STABILIZED NALOXONE FORMULATIONS

This is a continuation of application Ser. No. 08/319,920, filed Oct. 7, 1994, now abandoned.

FIELD OF THE INVENTION

The present invention relates to a pharmaceutical composition for administering naloxone by injection. More particularly, this invention provides solution formulations of naloxone having better physical and chemical stability than other known formulations of naloxone.

BACKGROUND OF THE INVENTION

Formulations of pharmaceutical compositions and processes for preparing them depend upon the properties of the active ingredient, the desired route of administration and the end use to be obtained.

Naloxone is a narcotic antagonist that prevents or reverses the effects of opioids. The compound and methods for its synthesis are described in U.S. Pat. No. 3,254,088. Its use as a narcotic antagonist is described in U.S. Pat. No. 4,267,182. A preferred route of administration of a narcotic antagonist is by the parenteral route (i.e. intravenous injection or infusion). The parenteral route of administration affords rapid delivery of the drug, complete bioavailability, and is more predictable and controllable than other routes. Solution formulations for parenteral administration must be essentially free of particulate matter, and they must be sterile. They must be physically and chemically stable, so that efficacy and safety are predictable.

Formulations for parenteral administration can be prepared as solutions that are ready to inject or ready to dilute with an infusion solution, or they can be prepared as dry powders that must be dissolved before use. Solution formulations are preferred over dry powders, when feasible, because of ease of use, ease of manufacture, and reduced cost.

U.S. Pat. No. 4,576,930 describes the stabilization of glucose solutions for intravenous infusion during autoclaving by addition of chelating agents, such as sodium edetate, to suppress thermal discoloration and decomposition of the glucose.

Instability of naloxone solution has been observed in the manufactured product. Autoclaving of currently available formulations of naloxone caused significant degradation of naloxone and formation of noroxymorphone. The degradation rates depended on headspace oxygen content. When non-autoclaved samples were sparged/flushed with nitrogen, no significant changes were observed in naloxone and bisnaloxone levels. However, noroxymorphone level increased from 0.08% to 0.4% over a six-week period at 60° C. It has now been found that addition of a chelating agent, such as sodium edetate, to the commercial formulation prevents naloxone degradation, even in the presence of oxygen and after autoclaving.

SUMMARY OF THE INVENTION

According to the present invention it has been discovered that pharmaceutical compositions of the drug naloxone can be prepared that have improved physical and chemical stability, can be autoclaved, do not require nitrogen sparging and are ready-to-use solutions. These pharmaceutical compositions are useful for intramuscular injection, intravenous injection or infusion to prevent or reverse the effects of opioid narcotics. More particularly, the compositions contain an effective amount of naloxone, an acidic or buffer component to give a pH of the final composition of 3–3.5, a stabilizing agent, and a tonicity-adjusting agent, said composition being autoclaved. Advantages of such a composition include, but are not limited to: ease of use, ease of manufacture, reduced cost and increased shelf-life.

BRIEF DESCRIPTION OF THE DRAWINGS

The invention will be further described in connection with the accompanying tables and figures, in which:

FIG. 2 is a graphical illustration of the noroxymorphone formation profiles for non-autoclaved naloxone solutions.

FIG. 3 is a graphical illustration of the noroxyrnorphone formation profile for naloxone solutions containing sodium edetate.

FIG. 4 is a graphical illustration of the noroxymorphone formation profile for naloxone solutions containing parabens.

FIG. 5 is a bar graph representation of the effect of the sodium edetate concentration on the stability of autoclaved and non-autoclaved nitrogen purged naloxone solutions.

FIG. 6 is a bar graph representation of the effect of the sodium edetate concentration on the stability of autoclaved and non-autoclaved naloxone solutions without nitrogen purging.

FIG. 7 is a graphical illustration of the effect of sodium edetate concentration on the stability of nitrogen purged naloxone solutions at 60° C.

FIG. 8 is a graphical illustration of the effect of sodium edetate concentration on the stability naloxone solutions at 60° C. without nitrogen purging.

DETAILED DESCRIPTION OF THE INVENTION

Figure 1A:
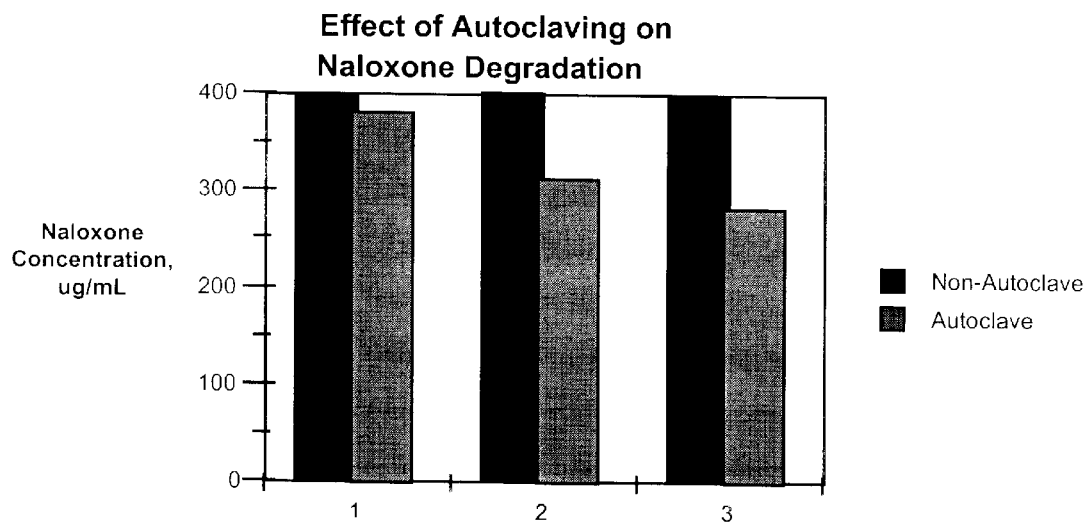
FIG. 1a is a bar graph representation of the effect of autoclaving on the degradation of naloxone in Formulation I.

Ready-to-use injectable solution formulations of naloxone with improved chemical and physical stability are preferably composed of an effective amount of naloxone hydrochloride, an acid or a buffer to yield a final solution pH of 3–3.5, one or more tonicity adjusting agents, and a stabilizing agent selected from sodium edetate, citrate and/or ethylenediamine tetraacetic acid and its other salts Said compositions are autoclaved for sterilization.

Preferred compositions use dilute hydrochloric acid, acetate, citrate or phophate to adjust the pH to 3–3.5. Specifically preferred compositions use dilute hydrochloric acid to adjust the pH to about 3.2. Preferred tonicity adjusting agents include sodium chloride, sorbitol or mannitol. The specifically preferred tonicity adjusting agent is sodium chloride. These compositions are preferably terminally sterilized by autoclaving. A typical autoclaving process is to expose the containers of the composition to steam under pressure for at least 15 minutes at a minimum temperature of 121° C.

The preferred concentration of naloxone in the composition is 0.01 to 10 mg/mL Specifically preferred are concentrations of 0.02 to 1 mg/mL. Preferred concentrations of the stabilizing agents are 0.0001 to 1% . Specifically preferred concentrations are 0.001 to 0.1%.

EXAMPLE 1

The chemical stability of naloxone was evaluated in solutions of varying compositions stored at pH 3.2 and 60° C. Three solution formulations (Tables I to III) were prepared in the presence and absence of parabens and sodium edetate.

TABLE I

Formulation I
Naloxone Solution (0.4 mg/mL)

| Ingredient | Amount per mL |
|---|---|
| Naloxone HCl | 0.4 mg |
| Sodium Chloride | 8.6 mg |
| Hydrochloric Acid, 0.1N, | as needed to pH 3.2 |
| Water For Injection | q.s. to 1 mL |

TABLE II

Formulation II
Naloxone Solution (0.4 mg/mL)
in the presence of Parabens

| Ingredient | Amount per mL |
|---|---|
| Naloxone HCl | 0.4 mg |
| Methylparaben | 1.8 mg |
| Propylparaben | 0.2 mg |
| Sodium Chloride | 8.6 mg |
| Hydrochloric Acid, 0.1N | as needed to pH 3.2 |
| Water For Injection | q.s. to 1 mL |

TABLE III

Formulation III
Naloxone Solution (0.4 mg/mL)
in the presence of sodium edetate

| Ingredient | Amount per mL |
|---|---|
| Naloxone HCl | 0.4 mg |
| sodium edetate | 1 mg |
| Sodium Chloride | 8.6 mg |
| Hydrochloric Acid, 0.1N | as needed to pH 3.2 |
| Water For Injection | q.s. to 1 mL |

The solutions were either not sparged/flushed, or sparged/flushed with oxygen or nitrogen, and then stored at 60° C. The impact of autoclaving on stability was examined by comparing the naloxone, noroxymorphone and bisnaloxone concentrations of autoclaved (15 minutes) and non-autoclaved samples. The study conditions are summarized in Table IV.

TABLE IV

Batch Numbers and conditions for
Naloxone Solutions Stability Studies

| Formulation I | Formulation II with Paraben | Formulation III with sodium edetate |
|---|---|---|
| XYZ* | XYZP* | XYZE* |
| NN5 | NN5P | NN5E |
| NA5 | AN5P | NA5E |
| AN5 | ON5P | AN5E |
| AA5 |  | AA5E |
| ON5 |  |  |
| OA5 |  |  |
| NN9 |  |  |
| NA9 |  |  |
| AN9 |  |  |
| AA9 |  |  |
| ON9 |  |  |
| OA9 |  |  |

*X- The first letter
• N for samples that were sparged and flushed with nitrogen;
• A for samples that were not sparged and flushed;
• O for samples that were sparged and flushed with oxygen.
Y- The second letter
• N represents samples that were not autoclaved
• A represents samples that were autoclaved.
Z- The third letter
• 5 represents 5 mL fill.
• 9 represents 9 mL fill.
P- Samples with parabens added
E- Samples with sodium edetate added At various time intervals, headspace oxygen content and concentrations of naloxone, noroxymorphone and bisnaloxone were monitored by Mocon/Toray Oxygen Headspace Analyzer (Model LC-700F), and an HPLC method, respectively.

Figure 1B:
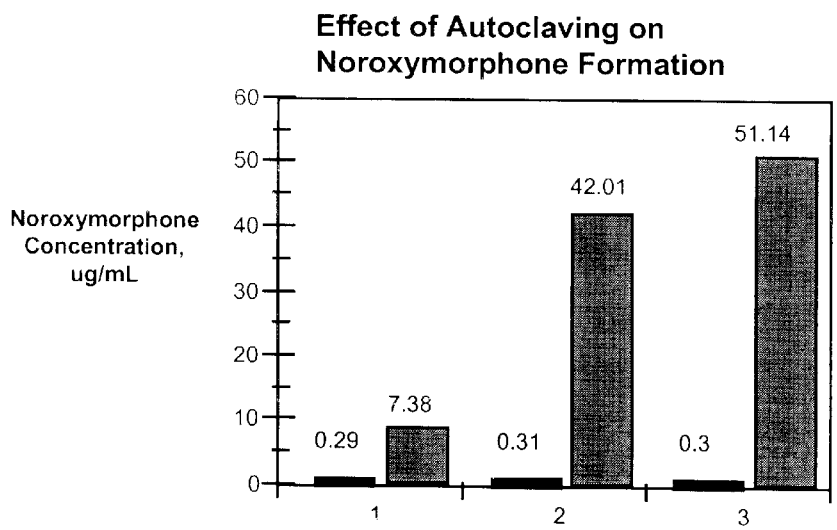
FIG. 1b is a bar graph representation of the effect of autoclaving on the formation of noroxymorphone in naloxone Formulation I.

Autoclaving of formulation I resulted in significant naloxone loss, and generated substantial amount of noroxymorphone (FIG. 1), especially in the presence of oxygen. In formulation I samples assayed initially after autoclaving, 4, 20 and 29% drug loss were observed for nitrogen flushed, non-flushed and oxygen flushed samples, respectively (Table V). From the mass balance and appearance of many extra peaks, it appears that naloxone also degraded to other unidentified compounds. However, formulation III which contained sodium edetate was stable after autoclaving.

TABLE V

Naloxone Solutions Stability at 60° C. Concentration, µg/mL

| | Initial | | | | 1 Week | | | |
|---|---|---|---|---|---|---|---|---|
| Sample** | Nalox. | Norox | Bisnal | $O_2$* | Nalox. | Norox | Bisnal | $O_2$* |
| Formulation I | | | | | | | | |
| NN5 | 398 | 0.29 | 0.46 | 3.8 | 409 | 0.43 | 1.06 | 3.2 |
| NA5 | 383 | 7.38 | 0.83 | 2.8 | 391 | 9.05 | 1.43 | 3.1 |
| AN5 | 399 | 0.31 | 0.48 | 17.6 | 409 | 0.74 | 1.27 | 17.6 |

TABLE V-continued

Naloxone Solutions Stability at 60° C. Concentration, μg/mL

| Sample | | | | | | | | |
|---|---|---|---|---|---|---|---|---|
| AA5 | 314 | 42.01 | 4.08 | 17.7 | 320 | 32.99 | 4.03 | 17.6 |
| ON5 | 398 | 0.30 | 0.57 | >50 | 404 | 0.93 | 1.71 | >50 |
| OA5 | 282 | 51.14 | 2.97 | >50 | 287 | 35.71 | 3.26 | >50 |
| NN9 | 401 | 0.27 | 0.56 | 4.6 | 412 | 0.48 | 1.08 | 4.6 |
| NA9 | 385 | 8.99 | 1.00 | 3.3 | 397 | 8.54 | 1.51 | 4.7 |
| AN9 | 400 | 0.25 | 0.49 | 17.9 | 410 | 0.73 | 1.26 | 17.9 |
| AA9 | 324 | 35.75 | 0.12 | 17.1 | 325 | 31.87 | 3.67 | 17.0 |
| ON9 | 398 | 0.29 | 0.49 | >50 | 405 | 0.98 | 1.75 | >50 |
| OA9 | 282 | 51.33 | 2.93 | >50 | 279 | 37.17 | 3.05 | >50 |
| Formulation II (parabens added) | | | | | | | | |
| NN5P | 407 | 0.11 | 2.17 | 3.1 | 408 | 0.27 | 2.62 | 2.8 |
| AN5P | 404 | 0.29 | 2.14 | 18.5 | 397 | 1.52 | 2.76 | 18 |
| ON5P | 404 | 0.28 | 2.17 | >50 | 401 | 3.67 | 3.28 | >50 |
| Formulation III (EDTA added) | | | | | | | | |
| NN5E | 396 | 0.32 | 0.13 | 3.2 | 391 | 0.10 | 1.04 | 2.7 |
| NA5E | 397 | 0.37 | 0.11 | 3.3 | 395 | 0.2 | 1.03 | 1.8 |
| AN5E | 397 | 0.34 | 0.12 | 17.4 | 397 | 0.12 | 1.10 | 18.1 |
| AA5E | 397 | 0.35 | 0.16 | 17.8 | 391 | 0.52 | 1.19 | 18.0 |

| | 2 Weeks | | | | 6 Weeks | | | |
|---|---|---|---|---|---|---|---|---|
| Sample** | Nalox. | Norox | Bisnal | $O_2$* | Nalox. | Norox | Bisnal | $O_2$* |
| Formulation I | | | | | | | | |
| NN5 | 413 | 0.76 | 1.09 | 2.8 | 400 | 1.35 | 0.53 | 2.5 |
| NA5 | 390 | 9.09 | 1.37 | 1.9 | 391 | 9.64 | 0.79 | 2.6 |
| AN5 | 399 | 1.0 | 1.15 | 16.9 | 382 | 3.15 | 1.02 | 16.7 |
| AA5 | 314 | 31.7 | 3.54 | 17.3 | 302 | 32.24 | 2.42 | 16.7 |
| ON5 | 403 | 1.63 | 2.01 | >50 | 371 | 6.16 | 1.93 | >50 |
| OA5 | 289 | 27.7 | 2.99 | >50 | 256 | 38.95 | 2.27 | >50 |
| NN9 | 412 | 0.81 | 1.12 | 2.3 | 417 | 1.59 | 0.64 | 4.1 |
| NA9 | 400 | 6.28 | 1.34 | 2.6 | 394 | 6.06 | 0.73 | 3.9 |
| AN9 | 401 | 0.98 | 1.42 | 17.5 | 387 | 3.09 | 1.00 | 16.4 |
| AA9 | 311 | 31.31 | 3.55 | 16.8 | 310 | 33.0 | 2.58 | 15.6 |
| ON9 | 403 | 1.59 | 2.02 | >50 | 366 | 6.27 | 1.95 | >50 |
| OA9 | 265 | 32.5 | 2.75 | >50 | 241 | 37.79 | 1.86 | >50 |
| Formulation II (parabens added) | | | | | | | | |
| NN5P | 402 | 0.78 | 1.89 | 1.6 | 409 | 1.40 | 0.50 | 2.1 |
| AN5P | 400 | 3.21 | 1.42 | 18 | 391 | 12.51 | 0.90 | 17.0 |
| ON5P | 408 | 7.58 | 1.99 | >50 | 381 | 41.07 | 1.43 | >50 |
| Formulation III (EDTA added) | | | | | | | | |
| NN5E | 391 | 0.16 | 0.93 | 1.5 | 395 | 0.62 | 0.37 | 2.1 |
| NA5E | 395 | 0.24 | 0.93 | 1.4 | 407 | 0.71 | 0.37 | 2.0 |
| AN5E | 397 | 0.19 | 0.94 | 17.7 | 408 | 0.73 | 0.60 | 17.0 |
| AA5E | 391 | 0.44 | 1.07 | 17.7 | 398 | 0.66 | 0.60 | 17.0 |

*The head space oxygen contents in the vials were determined using Mocon/Toray Oxygen Headspaoe Analyser. The Analyser can only accurately determine oxygen content less than 50%.
**Table IV summarizes the study condition for each sample.

Oxygen also enhanced naloxone degradation and noroxymorphone formation in non-autoclaved samples. About 4 and 8% drug loss were observed for non-flushed and oxygen flushed samples stored at 60° C. for six weeks. The amount of noroxymorphone generated depended on headspace oxygen content (FIG. 2).

The effect of addition of sodium edetate to stabilize naloxone formulations in the presence and absence of oxygen and with and without autoclaving is shown in FIG. 3. No significant changes in naloxone, noroxymorphone and bisnaloxone concentrations were observed by HPLC (Table V).

For the control samples (nitrogen sparged, non-autoclaved, and no sodium edetate or parabens added), no change in naloxone and bisnaloxone levels was observed, and noroxymorphone level increased slightly (from 0.08% to 0.4%) over a six-week period at 60° C.

In the presence of oxygen, parabens enhanced naloxone degradation and noroxymorphone formation, and the degradation rates depended on headspace oxygen content. Noroxymorphone levels rose to about 3 and 10% in non-flushed and oxygen flushed samples, respectively, after six-weeks storage at 60° C. (FIG. 4).

No differences in naloxone, noroxymorphone and bisnaloxone levels were observed for samples in 10 mL vials with 5 mL and 9 mL fill (first two sets of data in Table V).

The headspace oxygen contents for nitrogen sparged/flushed and non-sparged samples were 3–5% and 18%, respectively.

EXAMPLE 2

Solution stability of naloxone hydrochloride in the presence of various sodium edetate concentrations were investigated to determine the lower range of sodium edetate concentration that effectively stabilizes naloxone in solution. Naloxone formulations (Table VI) with sodium edetate at concentration of 0.00005% to 0.001% were prepared. The solutions were either not sparged/flushed, or sparged/flushed with nitrogen, and then stored at 60° C. At various time intervals, concentrations of naloxone, noroxymorphone and bisnaloxone were monitored by an HPLC method. Since percentage of naloxone loss is relatively small, in some cases, they are within the HPLC variation, degradants were followed for degradation indication. The stabilization effect of sodium edetate on naloxone upon autoclaving was examined by comparing the naloxone, noroxymorphone and bisnaloxone concentrations of autoclaved (15 minutes) and non-autoclaved samples.

TABLE VI

Naloxone Solution (0.4 mg/mL) Formulations

| Ingredient | Amount per mL |
|---|---|
| Naloxone HCl | 0.4 mg |
| sodium edetate | * |
| Sodium Chloride | 8.6 mg |
| Hydrochloric Acid, 0.1N | as needed to pH 3.2 |
| Water For Injection | q.s. to 1 mL |

*Formulation I: no sodium edetate added;
Formulation IV: 0.01 mg/mL of sodium edetate added;
Formulation V: 0.001 mg/mL of sodium edetate added;
Formulation VI: 0.0005 mg/mL of sodium edetate added.

Autoclaving of solution without the addition of sodium edetate (formulation I) resulted in naloxone loss, and generation of noroxymorphone and bisnaloxone (Table VII, formulation I). Further increase of noroxymorphone was observed at 60° C. for four weeks.

TABLE VII

Naloxone Solution Stability in The Presence of Different Sodium edetate Concentration at 60° C.
Concentration, μg/mL

| Sample XYZ* | Initial | | | 4 Week | | | 6 Week | | |
|---|---|---|---|---|---|---|---|---|---|
| | Nalox. | Norox | Bisnal | Nalox. | Norox | Bisnal | Nalox. | Norox | Bisnal |
| Formulation (no sodium edetate added) | | | | | | | | | |
| NNC | 374 | 0.66 | 0.37 | 370 | 0.93 | 0.53 | 369 | 0.95 | 0.46 |
| NAC | 366 | 2.83 | 1.33 | 362 | 3.55 | 1.46 | 364 | 3.80 | 1.37 |
| ANC | 363 | 0.61 | 0.37 | 361 | 1.30 | 0.59 | 360 | 1.41 | 0.60 |
| AAC | 360 | 2.49 | 1.24 | 355 | 3.69 | 0.96 | 359 | 3.74 | 0.90 |
| Formulation A (0.001% sodium edetate added) | | | | | | | | | |
| NNE-A | 379 | 0.42 | 0.44 | 378 | 0.72 | 0.34 | 377 | 0.33 | 0.34 |
| NAE-A | 380 | 0.36 | 0.43 | 376 | 0.72 | 0.37 | 387 | 0.37 | 0.35 |
| ANE-A | 371 | 0.39 | 0.43 | 376 | 0.72 | 0.37 | 374 | 0.37 | 0.35 |
| AAE-A | 371 | 0.38 | 0.42 | 371 | 0.75 | 0.37 | 378 | 0.42 | 0.36 |
| Formulation B (0.0001% sodium edetate added) | | | | | | | | | |
| NNE-B | 364 | 0.68 | 0.35 | 365 | 0.45 | 0.41 | 363 | 0.43 | 0.36 |
| NAE-B | 366 | 0.90 | 0.45 | 366 | 0.83 | 0.43 | 364 | 0.82 | 0.38 |
| ANE-B | 377 | 0.71 | 0.35 | 370 | 0.84 | 0.54 | 371 | 0.83 | 0.07 |
| AAE-B | 372 | 1.90 | 0.56 | 364 | 2.60 | 0.63 | 367 | 2.70 | 0.60 |
| Formulation C (0.00005% sodium edetate added) | | | | | | | | | |
| NNE-C | 404 | 0.76 | 0.38 | 402 | 0.48 | 0.41 | 398 | 1.05 | 0.41 |
| NAE-C | 401 | 1.93 | 0.56 | 399 | 2.24 | 0.60 | 394 | 1.91 | 0.49 |
| ANE-C | 402 | 0.80 | 0.37 | 396 | 1.29 | 0.65 | 390 | 1.69 | 0.81 |
| AAE-C | 398 | 2.60 | 1.22 | 388 | 3.50 | 0.79 | 388 | 3.56 | 0.92 |

*The letter code for the samples:
XYZ - X, N: nitrogen purged; A: air, non-nitrogen purged. - Y, N: non-autoclaved; A: autoclaved. - Z, C: control (no sodium edetate added); E: sodium edetate added at concentration indicated.

No significant increase of noroxymorphone was observed for a naloxone composition purged with nitrogen and in the presence of sodium edetate at concentration of 0.0001% and higher after autoclaving (FIG. 3). However, FIG. 5 shows that for a solution without nitrogen purging, the presence of sodium edetate at concentration of 0.0001% is not sufficient to prevent the formation of noroxymorphone during autoclaving.

Sodium edetate at a concentration of 0.0001% combined with nitrogen purging can stabilize naloxone at 60° C. over a six-week period (FIG. 6). However, an increase in noroxymorphone was observed for non-nitrogen purged and autoclaved solutions at 60° C. for six weeks (FIG. 7).

Sodium edetate at a concentration of 0.001% effectively protected naloxone from heat degradation (autoclaving and at 60° C.). However, nitrogen purge is needed to stabilize naloxone solution containing 0.0001% of sodium edetate during autoclaving. No stabilization effect was observed for solutions with sodium edetate at concentration of 0.00005% and below.

What is claimed:

1. A parenteral pharmaceutical composition autoclaved for sterilization, wherein the pH is about 3.0–3.5, comprising:
   a) an effective amount of 4,5-epoxy-3,14-dihydroxy-17-(2-propenyl)morphinan-6-one;
   b) a suitable acidic or buffer component;
   c) a stabilizing agent; and
   d) a tonicity adjusting agent.

2. The pharmaceutical composition of claim 1 wherein the pH is about 3.2.

3. The pharmaceutical composition of claim 1, wherein the component (b) is selected from the group consisting of aqueous hydrochloric acid, citrate, acetate and phosphate.

4. The pharmaceutical composition of claim 1, wherein the component (c) is selected from the group consisting of citric acid, ethylenediaminetetraacetic acid, and their pharmaceutically acceptable salts.

5. The pharmaceutical composition of claim 1, wherein the component (d) is selected from the group consisting of sodium chloride, sorbitol and mannitol.

6. The pharmaceutical composition of claim 1 wherein component (a) is present in an amount to be delivered of about 0.01 to 10 mg/mL.

7. The pharmaceutical composition of claim 1 wherein component (c) is present in a concentration of about 0.0001 to 1%.

8. The pharmaceutical composition of claim 1 wherein component (a) is present in an amount of about 0.02 to 1 mg/mL, and component (b) is present in amount to yield a pH of about 3.2 and component (c) is present in a concentration of about 0.001 to 0.1%.

9. The pharmaceutical composition of claim 1 wherein component (b) is dilute hydrochloric acid, and component (c) is sodium edetate and component (d) is sodium chloride.

* * * * *